United States Patent
Jena et al.

(10) Patent No.: US 9,416,016 B2
(45) Date of Patent: Aug. 16, 2016

(54) HYPERHALOGENS AND HIGHLY ELECTRONEGATIVE COMPOSITIONS

(75) Inventors: Puru Jena, Richmond, VA (US); Gerd Gantefoer, Constance (DE)

(73) Assignee: Virginia Commonwealth University, Richmond, VA (US)

( * ) Notice: Subject to any disclaimer, the term of this patent is extended or adjusted under 35 U.S.C. 154(b) by 415 days.

(21) Appl. No.: 13/820,574

(22) PCT Filed: Sep. 8, 2011

(86) PCT No.: PCT/US2011/050788
§ 371 (c)(1),
(2), (4) Date: Mar. 4, 2013

(87) PCT Pub. No.: WO2012/033893
PCT Pub. Date: Mar. 15, 2012

(65) Prior Publication Data
US 2013/0156866 A1    Jun. 20, 2013

Related U.S. Application Data

(60) Provisional application No. 61/380,768, filed on Sep. 8, 2010.

(51) Int. Cl.
*A01N 59/16* (2006.01)
*A01N 59/20* (2006.01)
*A61K 33/34* (2006.01)
*C01B 35/10* (2006.01)
*C01B 35/12* (2006.01)
*A61K 33/24* (2006.01)
*C09K 3/00* (2006.01)

(52) U.S. Cl.
CPC ............ *C01B 35/1027* (2013.01); *A01N 59/16* (2013.01); *A01N 59/20* (2013.01); *A61K 33/24* (2013.01); *A61K 33/34* (2013.01); *C01B 35/127* (2013.01); *C09K 3/00* (2013.01)

(58) Field of Classification Search
CPC ....... A01N 59/16; A01N 59/20; A61K 33/24; A61K 33/34; C01B 35/1027; C01B 35/127; C09K 3/00
See application file for complete search history.

(56) References Cited

PUBLICATIONS

Gotz, M. "Origin of hte Unusual Properties of Aun(BO)2 Clusters", ChemPhysChem, Feb. 23, 2010, vol. 11, p. 853-858.*
Gotz et al. ChemPhysCHem, Feb. 23, 2010, vol. 11, p. 853.*
Kandalam et al. "Hyperhalogens: Discovery of a New Class of Highly Electronegative Species", Angew. Chem. Int. Ed., 49, 8966, published online Oct. 6, 2010.*
Virginia Commonwealth University, "New Class of highly electronegative chemical species discovered", published Oct. 17, 2010, Science daily, accessed online May 21, 2015. www.sciencedaily.com/releases/2010/10/101008162702.htm>.*
Willis et al.; "Hyperhalogens: Discovery of a New Class of Highly Electronegative Species"; Angew. Chem, Int. Ed., Oct. 6, 2010, vol. 49, pp. 8966-8970.
Feng et al.; "Structures and Photoelectron Spectroscopy of Cun(BO2)m-(n, m=1, 2) Clusters: Observation of Hyperhalogen Behavior"; The Journal of Chemical Physics, Mar. 3, 2011, vol. 134, 094309.
Gotz et al.; "Origin of the Unusual Properties of Aun(BO2) Clusters"; ChemPhysChem, Feb. 23, 2010, vol. 11, pp. 853-858.
Zhai et al.; "Vibrationally Resolved Photoelectron Spectroscopy of BO- and BO2-: A Joint Experimental and Theoretical Study"; J. Phys. Chem., 2011, vol. 111, pp. 1030-1035.

* cited by examiner

*Primary Examiner* — Audrea Buckley
(74) *Attorney, Agent, or Firm* — Whitham, Curtis & Cook, P.C.

(57) ABSTRACT

Hyperhalogens, a new class of highly electronegative species, are now invented. A hyperhalogen is a superhalogen-containing composition in which the electron affinity (EA) of the hyperhalogen is even larger than that of the superhalogens they are composed of. Novel production methods are provided in which highly electronegative species are produced by surrounding a central metal atom by superhalogen moieties.

10 Claims, 5 Drawing Sheets

| Clusters | ADE (eV) | | VDE (eV) | |
| --- | --- | --- | --- | --- |
| | Expt | Theo | Expt | Theo |
| AuO[24] | 2.378 | | 2.378 | 2.31 |
| AuO$_2$[24] | 3.40 | | 3.40 | 3.47 |
| Au(BO$_2$) | 2.8 | 3.06 | 3.0 | 3.34 |
| AuO(BO$_2$) | 4.0 | 4.21 | 4.4 | 4.42 |
| Au(BO$_2$)$_2$ | 5.7 | 5.54 | 5.9 | 5.86 |
| Au$_3$(BO$_2$) | 3.1 | 3.00 | 3.2 | 3.36 |
| Au$_3$O(BO$_2$) | 4.9 | 4.86 | 5.2 | 5.01 |

HYPERHALOGENS AND HIGHLY ELECTRONEGATIVE COMPOSITIONS

CROSS-REFERENCE TO RELATED APPLICATIONS

This application is a national-stage Patent Cooperation Treaty (PCT) filing from 'PCT/US2011/050788 filed Sep. 8, 2011, and this application claims priority to U.S. Provisional Applications 61/380,768 filed Sep. 8, 2010. The complete contents of these applications is herein incorporated by reference.

STATEMENT OF GOVERNMENT INTEREST

This invention was made with support in part from grants from the Department of Energy (DE-FG02-96ER45579) and from Defense Threat Reduction Agency (Department of Defense) (HDTRA1-09-1-0025 and HDTRA1-10-C-0013), and the U.S. Government may have certain rights in the invention.

FIELD OF THE INVENTION

This invention relates to halogen-containing compositions, especially highly electronegative halogen-containing compositions.

BACKGROUND OF THE INVENTION

Halogen atoms because of their large electron affinity are known to be reactive and play a major role in chemistry.

There has existed another class of molecules which possess electron affinities that are larger than those of any halogen atom. These molecules called superhalogens consist of a central atom, typically a metal, surrounded by halogen or oxygen atoms.

Electron affinity (EA), defined as the amount of energy necessary to remove an electron from an anion, plays a dominant role in reactivity. This is evidenced by halogen atoms whose electron affinities are larger than those of any other element in the periodic table. Halogen atoms such as F, Cl, and Br are among the most electronegative elements in the periodic table; they are very reactive and form salts. They possess rather large electron affinity (EA) which is defined as the energy gained when an extra electron is attached to these atoms. Cl has the highest electron affinity, namely, 3.6 eV.

There exists a class of molecules whose electron affinities are even larger than those of halogen atoms. Bartlett and collaborators were among the first to study such molecules nearly half a century ago. They showed that $PtF_6$ can even oxidize $O_2$ molecule [1] and Xe atom [2]. Several years later Gutsev and Boldyrev coined the word superhalogen to describe these highly electronegative species [3]. According to these authors, a superhalogen consists of a central metal atom surrounded by halogen atoms. When the number of these halogen atoms exceeds the maximal valence of the metal atom, the molecule possesses electron affinities that are much larger than that of the halogen atoms. In a series of subsequent theoretical studies, Boldyrev and collaborators showed that a large number of superhalogens, where the central metal atom is typically a sp element, are possible [4-8]. The first photoelectron spectrum of $MX_2^-$ (M=Li, Na; X=Cl, Br, and I) was reported by Wang and co-workers [9]. Subsequent photoelectron spectroscopic studies and theoretical studies have further confirmed the existence of superhalogens in the gas-phase [10-14]. In a theoretical study, it was proposed that hydrogen atom can act as the "central atom" to form a superhalogen and it was shown that the vertical detachment energies of $[H_nF_{n+1}]^-$ can be extremely high [15]. Numerous other superhalogen anions, such as permanganate $(MnO_4^-)$ [16], perchlorate $(ClO_4^-)$, hexafluoride $(AuF_6^-$ and $PtF_6^-)$ [17-18], $BO_2^-$ [19], $Mg_xCl_y^-$ [20] have also been reported. Because of their high EAs, superhalogens almost always exist as negative ions, usually as the anionic portions of salts. Since salts composed of superhalogens generally have a high oxidative property, there is considerable interest in the synthesis of species with high EAs.

SUMMARY OF THE INVENTION

We have invented hyperhalogens, a new class of highly electronegative species. A hyperhalogen comprises a metal atom at the core surrounded by superhalogen molecules. The hyperhalogens can have superoxidizing properties and can be used in a number of technologies including air purification and biological decontamination.

The invention provides a new class of molecules/clusters that are highly electronegative.

We have invented a novel method of designing a new class of highly electronegative clusters, where the central metal atom is surrounded by the superhalogen units, rather than the halogen atoms. This new class of species has EAs even larger than that of the superhalogens they are composed of.

In a preferred embodiment, the invention provides a hyperhalogen composition, comprising: at least one superhalogen, wherein the hyperhalogen composition has an EA higher than an EA of the at least one superhalogen included therein, such as, e.g., an inventive hyperhalogen that comprises superhalogens, wherein the hyperhalogen composition has an EA higher than an EA of at least one or all superhalogen(s) included therein; an inventive hyperhalogen composition wherein the EA of the hyperhalogen composition is at least 1 eV higher than the EA of at least one or all superhalogen(s) included therein; an inventive hyperhalogen that is Au-based; an inventive hyperhalogen that is Cu-based; an inventive hyperhalogen that comprises a core that is a metal atom; etc.

The invention in another preferred embodiment provides an electronegative composition comprising $BO_2$ and having an EA of substantially greater than 4.32 eV (such as, e.g., EA above 5 eV, EA of 5.54 eV, etc.), such as, e.g., inventive electronegative compositions comprising a central metal core; etc.

In another preferred embodiment, the invention provides a stable ternary nanocluster comprising superhalogen units as blocking blocks, wherein the nanocluster has an electron affinity larger than an electron affinity of any superhalogen making up the nanocluster; such as, e.g., inventive stable ternary nanoclusters comprising a central metal core (such as Au, Cu, etc.); etc.

The invention in another preferred embodiment provides a method of obtaining an increased EA for a superhalogen building block, comprising: substituting the superhalogen building block (such as, e.g., a superhalogen building block that is $BO_2$) for an oxygen atom contained in a cluster to produce a hyperhalogen that has an EA of at least 1 eV greater than the EA of the superhalogen building block. The invention in another preferred embodiment provides for use of a superhalogen in combination with a central metal core (such as, e.g., a central metal core that is Au or Cu, etc.), preferably use whereby an EA is provided that is greater (such as, e.g., 1 eV greater than for the superhalogen.

Further in another preferred embodiment, the invention provides a method of producing a composition with high-EA, comprising: providing a starting material that includes at least one oxygen atom, and substituting a replacement component (such as, e.g., a superhalogen) for an oxygen atom in the starting material, wherein one oxygen or plural oxygen atoms may be replaced, to produce the composition with high-EA (such as, e.g., a composition with an EA greater than an EA of the starting material).

The invention in another preferred embodiment provides a method of producing a highly electronegative composition, comprising: decorating a metal moiety (such as, e.g., a metal atom) with superhalogens to produce the highly electronegative composition, such as, e.g., inventive methods including decorating the metal atom with superhalogens to produce a composition with greater EA than an EA of at least one or all superhalogen(s) used in the decorating step.

In another preferred embodiment, the invention provides a composition comprising $Au(BO_2)_2$ or a derivative thereof, such as, e.g., an inventive composition wherein Au is in a central position between two $(BO_2)$ moieties. In a theoretical study, the current authors reported unusually stable $Au_n(BO_2)$ clusters, which exhibit superhalogen characteristics [21].

The invention in another preferred embodiment provides a composition comprising $Au_3O(BO_2)$ or a derivative thereof.

The invention in another preferred embodiment provides a composition comprising $Cu((BO_2)_2$ or a derivative thereof.

DESCRIPTION

Inventive compositions with high EA, relative to superhalogens, are provided. The invention is based on a discovery, by the present inventors, of a new class of stable ternary nanoclusters with superhalogen units as building blocks, whose electron affinities can be larger than even the superhalogens that make up these clusters. These new nanoclusters, called hyperhalogens, can be better oxidizing agents than the traditional superhalogens.

The hyperhalogen clusters, due their high electron-affinity, will exist as negatively charged ions and thus are useable as building blocks to synthesize inventive super-oxidizing agents.

Depending on the nature of central metal atom/core of the hyperhalogen, these species can carry a sizeable magnetic moment and can be novel magnetic materials with hyperhalogen building blocks. Examples of uses of negatively charged molecules are, e.g., as air purifiers, oxidizers, improving hygiene, etc. In addition, there is evidence that negatively charged molecules promote release of serotonin in the blood and hence can help treat depression. Examples of uses for the invention include, e.g., disinfectants, air cleaners, mood enhancers, etc.

Example 1

Figures 5, 6:
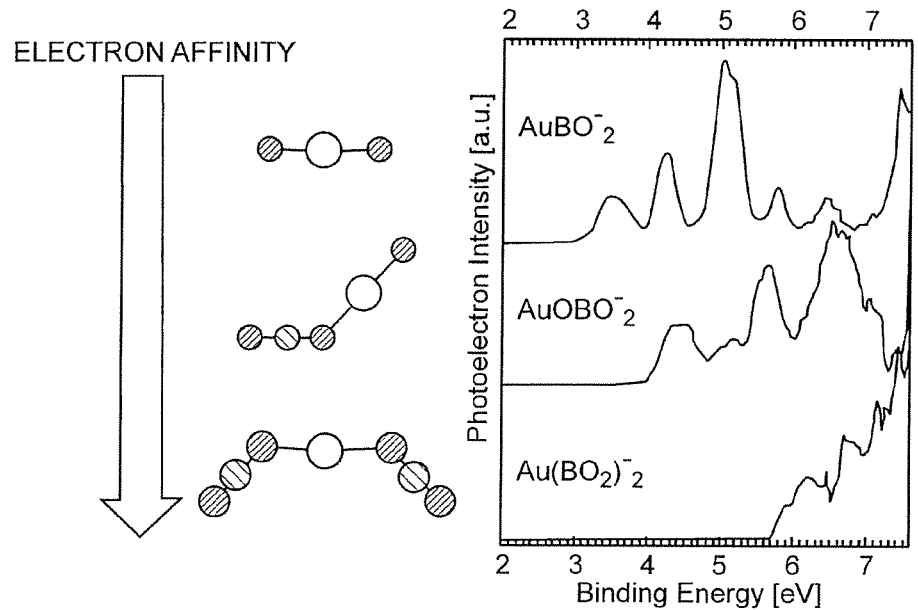
FIG. 5, which includes a graph which includes photoelectron spectra, illustrates the increasing EA (electron binding energy) with sequential replacement of the oxygen atoms with $BO_2$ units, finally resulting in the hyperhalogen.
FIG. 6 is a table of experimental threshold (ADE) and vertical detachment energies (VDE) along with the calculated ADE and VDE of the $[Au_n(BO_2)]^-$, $[Au_nO(BO_2)]^-$, and $[Au(BO_2)_2]^-$ clusters. The experimental uncertainty is ±0.1 eV.

In this example, Au was the central metal atom and $BO_2$ was the superhalogen building block. When the oxygen atoms in the $AuO_2$ cluster were sequentially replaced with $BO_2$ units, the EA of the resulting cluster increased continuously and for $Au(BO_2)_2$ cluster, the EA was as high as 5.54 eV. This EA is much larger than the EA of $BO_2$ (4.32 Ev), the superhalogen building unit of this species. FIG. 5 illustrates the increasing EA (electron binding energy) with sequential replacement of the oxygen atoms with $BO_2$ units, finally resulting in the hyperhalogen.

Example 2

In this example, a hyperhalogen was constructed by replacing the central metal atom with a multi-metal core. The Au atom was replaced with $Au_3$ cluster in $AuO(BO_2)$ species. The resulting $Au_3O(BO_2)$ has an EA larger than the $BO_2$ unit, thus making it a hyperhalogen. The results of theoretical calculations were validated by carrying out experimental studies.

Thus, based on this discovery, a whole new series of highly electronegative species can be synthesized by manipulating the central metal core as well as the superhalogen building blocks.

Example 3

A CU-borate $[Cu((BO_2)_2]$ was experimentally observed in gas-phase.

Example 4

In this example, we show that a new class of highly electronegative species can be synthesized if the peripheral halogen atoms are replaced by superhalogen moieties. We name this new class of electronegative species "hyperhalogens" because their electron affinities can even be larger than those of their superhalogen building blocks and hence can serve as ingredients in the synthesis of new superoxidizing agents.

Using density functional theory (DFT) and photoelectron spectroscopy (PES) experiments we demonstrate this by concentrating on an Au atom as well as an Au cluster decorated with $BO_2$ superhalogens. $BO_2$ molecule, like $MnO_4$, has a large electron affinity of 432 eV [19, 21], while its anionic counterpart, $BO_2^-$ being iso-electronic with $CO_2$, is a very stable anion.

It has been shown recently that the EA of a $XF_n$ (X=Cu—Au, n=1-6) cluster increases as the central coinage metal atom, is decorated successively with F atoms [22, 23]. This happens as the extra electron is delocalized over several halogen atoms. We questioned whether the electron affinity would increase even further if the metal atom is decorated with superhalogen molecules instead. Note that in this case the extra electron will be delocalized over superhalogen moieties. We considered what would happen if one were to replace some but not all of the halogens atoms with superhalogen molecules; whether the electron affinity would lie in between the two (for example, whether the electron affinity of $Au(BO_2)_2$ would be much larger than that of $AuO_2$; similarly, whether the electron affinity of AuO(BO$_2$) would be in between that of AuO$_2$ and Au(BO$_2$)$_2$).

Results and Discussion

From our DFT based calculations (see the table in FIG. 6) we found that the electron affinity of Au(BO$_2$)$_2$ is 5.54 eV which is 1.6 times larger than that of AuO$_2$ [24]. On the other hand, the electron affinity of AuO(BO$_2$) is 4.21 eV which lies between that of AuO$_2$ and Au(BO$_2$)$_2$. These results are validated by our photoelectron spectroscopy measurements. The fact that the electron affinities of superhalogens can be further enhanced by modifying the building blocks provides a new method for designing highly electronegative species. By suitably choosing the composition of these hyperhalogens and corresponding cations, new materials can be designed and synthesized with unique properties. In the following we provide details of our computational and experimental results.

(a) AuO, AuO$_2$ vs Au(BO$_2$), Au(BO$_2$)$_2$, and AuO(BO$_2$) Clusters

The electron affinity and vertical detachment energies of AuO and AuO$_2$ have been reported earlier by both experimental and theoretical groups [24-27]. According to the most recent work, AuO has an EA of 2.378 eV and the VDE of AuO$^-$ is also measured as 2.378 eV, while the theoretical calculations carried out at CCSD(T) level gave a VDE of 2.312 eV [24]. We use these reported values for comparison with the corresponding values for Au(BO$_2$)$_n$ (n=1-2) and AuO(BO$_2$) clusters in our table (FIG. 6).

First we discuss the electron affinity of AuO and Au(BO$_2$). As the O atom is replaced by BO$_2$ in AuO, the electron affinity of the resultant Au(BO$_2$) cluster increases to 2.8 eV (see FIG. 6). Similarly, a comparison of the VDE of (AuO)$^-$ and [Au(BO$_2$)]$^-$ clusters show that the replacement of O with BO$_2$ results in an increase of 0.6 eV, from 2.378 eV to 3.0 eV. This is in spite of the fact that Au(BO$_2$) is a closed shell system while AuO is an open shell system. Even though neither AuO nor Au(BO$_2$) is a superhalogen, it is important to note that replacing an electronegative atom, O, by a superhalogen, BO$_2$, leads to a significant increase in electron affinity. This will be shown, below, to play a major role.

We next consider AuO$_2$ and Au(BO$_2$)$_2$ clusters. The latter is formed by replacing two O atoms with two BO$_2$ superhalogen moieties. The electron affinity of AuO$_2$ was reported to be 3.40 eV which is larger than that of AuO [24]. Strikingly, the electron affinity of Au(BO$_2$)$_2$ is 5.7 eV which is substantially larger than that of AuO$_2$ and Au(BO$_2$) (see FIG. 6). Similarly, the VDE of [Au(BO$_2$)$_2$]$^-$ is 5.9 eV, while the VDE of [AuO$_2$]$^-$ was reported as 3.40 eV. Given the fact that BO$_2$ behaves as a monovalent species, while O is divalent, one may wonder if the comparison of the EA between AuO$_2$ and Au(BO$_2$)$_2$ is meaningful. In order to address this issue and have a better comparison, we have considered monovalent species, namely halogens as the ligands. We calculated the EA values of AuX$_2$, (X=F, Cl, Br, and I) and compared them with that of Au(BO$_2$)$_2$ cluster. Note that in both AuX$_2$ and Au(BO$_2$)$_2$, the Au atom is in the same oxidation state. Our calculated EA values of AuF$_2$, AuCl$_2$, AuBr$_2$, and AuI$_2$ molecules are 4.84 eV, 4.63 eV, 4.46 eV, and 4.38 eV, respectively, which are in good agreement with previous experimental and theoretical studies [28, 29]. It is observed that the EA values of AuX$_2$ molecules are significantly smaller than that of the corresponding theoretical EA (5.54 eV) of Au(BO$_2$)$_2$ cluster. We, therefore, term Au(BO$_2$)$_2$ as a hyperhalogen since its electron affinity is significantly increased by replacing the peripheral O atoms (in AuO$_2$) or halogen atoms (in AuX$^2$) with the superhalogen moiety, BO$_2$.

Figure 1:
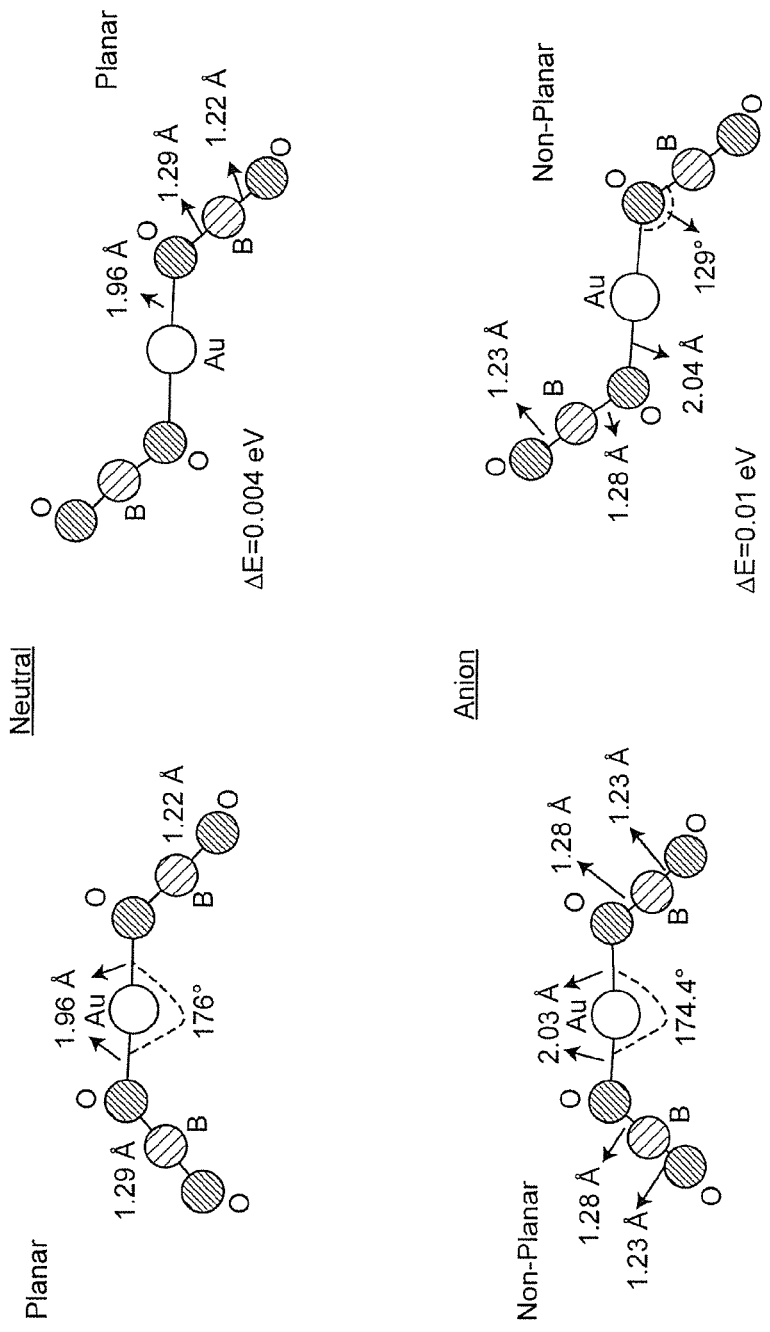
FIG. 1 depicts geometries of the ground state and next higher energy isomers of neutral and negatively charged [Au$(BO_2)_2$] clusters.

Regarding the properties of the Au(BO$_2$)$_2$ hyperhalogen we first discuss the ground state geometries of its neutral and anionic configurations given in FIG. 1. We found two energetically degenerate structural isomers having cis and trans form for both the neutral and anionic species. Note that in these two isomers the geometry of BO$_2$ moieties remains unaltered from its isolated state [19, 21]. The neutral Au(BO$_2$)$_2$ cluster is an open-shell system, with a doublet (2S+1=2) spin multiplicity. The natural bond orbital (NBO) charge analysis of the neutral cluster clearly showed that there is a charge transfer from the Au atom to both BO$_2$ moieties, resulting in a charge of +0.92e on the Au atom, and a charge of −0.46e on each of the BO$_2$ moieties. However, each BO$_2$ moiety requires one electron to be stabilized. Thus, the neutral Au(BO$_2$)$_2$ cluster lacks one electron, similar to that of a halogen atom.

Figure 2:
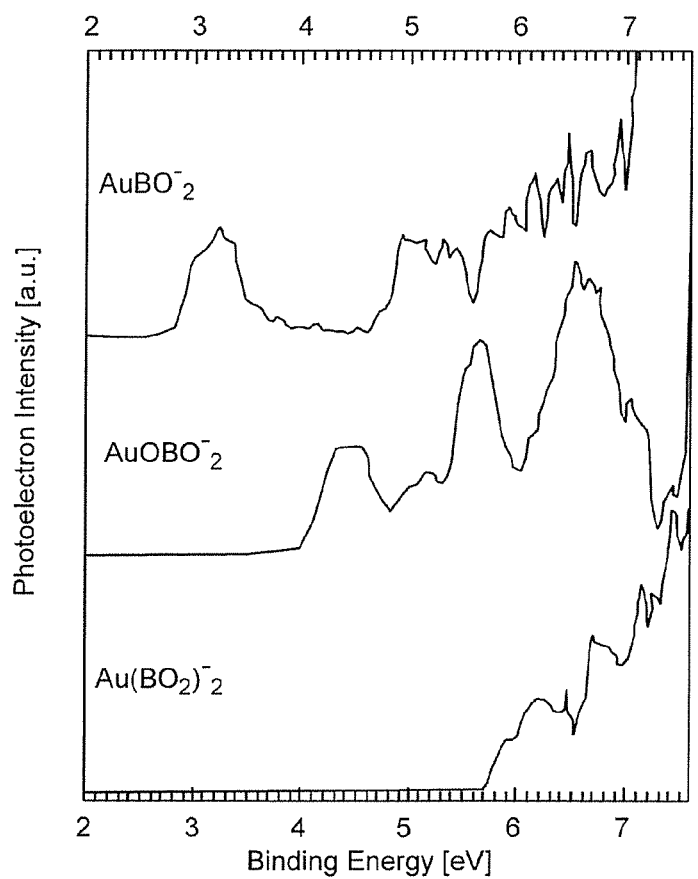
FIG. 2 is a graph which is a comparison of photoelectron spectra of $[Au(BO_2)]^-$, $[AuO(BO_2)]^-$, and $[Au(BO_2)_2]^-$ clusters.

The [Au(BO$_2$)$_2$]$^-$ cluster is a closed-shell system with a large HOMO-LUMO gap of 5.68 eV. The unusually large HOMO-LUMO gap, electronic shell closure, and the large binding energy of the extra electron (EBE or VDE) makes the [Au(BO$_2$)$_2$]$^-$ cluster a very stable anion, ideal for making a salt. The NBO charge analysis shows that the extra electron is delocalized over the entire cluster, thereby stabilizing both the BO$_2$ moieties as well as the entire [Au(BO$_2$)$_2$]$^-$ cluster. The VDE's of both isomers of [Au(BO$_2$)$_2$]$^-$ cluster are calculated to be 5.66 eV and 5.62 eV, respectively. The FES of the [Au(BO$_2$)$_2$]$^-$ cluster obtained from our experiments is shown in FIG. 2 and compared with that of [Au(BO$_2$)]$^-$ and [AuO(BO$_2$)]$^-$. The experimental electron affinity of [(AuBO$_2$)$_2$] is estimated to be 5.7 eV, while the measured VDE is 5.9 eV. The calculated VDEs for both the isomers are in good agreement with the measured value (5.9 eV±0.1 eV) in the Table (FIG. 6). Therefore, one cannot rule out the possibility that both these isomers could be present in the cluster beam. The enhanced stability of [Au(BO$_2$)$_2$]$^-$ is thus reflected in the PES as large VDE and EA values. This is further confirmed by studying the thermodynamic stability of the Au(BO$_2$)$_2$ cluster, namely by calculating the energy required to fragment the cluster into smaller stable clusters. The binding energy of Au(BO$_2$)$_2$ measured with respect to Au(BO$_2$) and BO$_2$ is 2.09 eV. The binding energy of [Au(BO$_2$)$_2$]$^-$ measured with respect to Au(BO$_2$) and BO$_2^-$ is 3.31 eV and with respect to [Au(BO$_2$)]$^-$ and BO$_2$ is 4.57 eV. Thus, the hyperhalogen Au(BO$_2$)$_2$ not only possesses anomalously large electron affinity, but also has a very stable anion.

Because Au can exist in an oxidation state of +3, one would expect Au(BO$_2$)$_4$ to also have larger electron affinity than, say AuF$_4$. To examine this, we computed the equilibrium geometries of neutral and anionic Au(BO$_2$)$_4$. Two nearly degenerate structures were found for the anionic Au(BO$_2$)$_4$; one having the shape of a crossed structure with bent arms and the other in the form where O—Au—O is bonded to a B$_4$O$_6$ structure. The vertical and adiabatic detachment energies of the former isomer are, respectively, 7.13 eV and 7.10 eV. Note that the electron affinity of AuF$_4$ is calculated to be 6.84 eV [23]. It is to be noted here that the crossed structure with bent arms is similar to the previously reported [30] Au(N$_3$)$_4^-$ unit in Ammonium Tetraazidoaurates (III).

Figure 3:
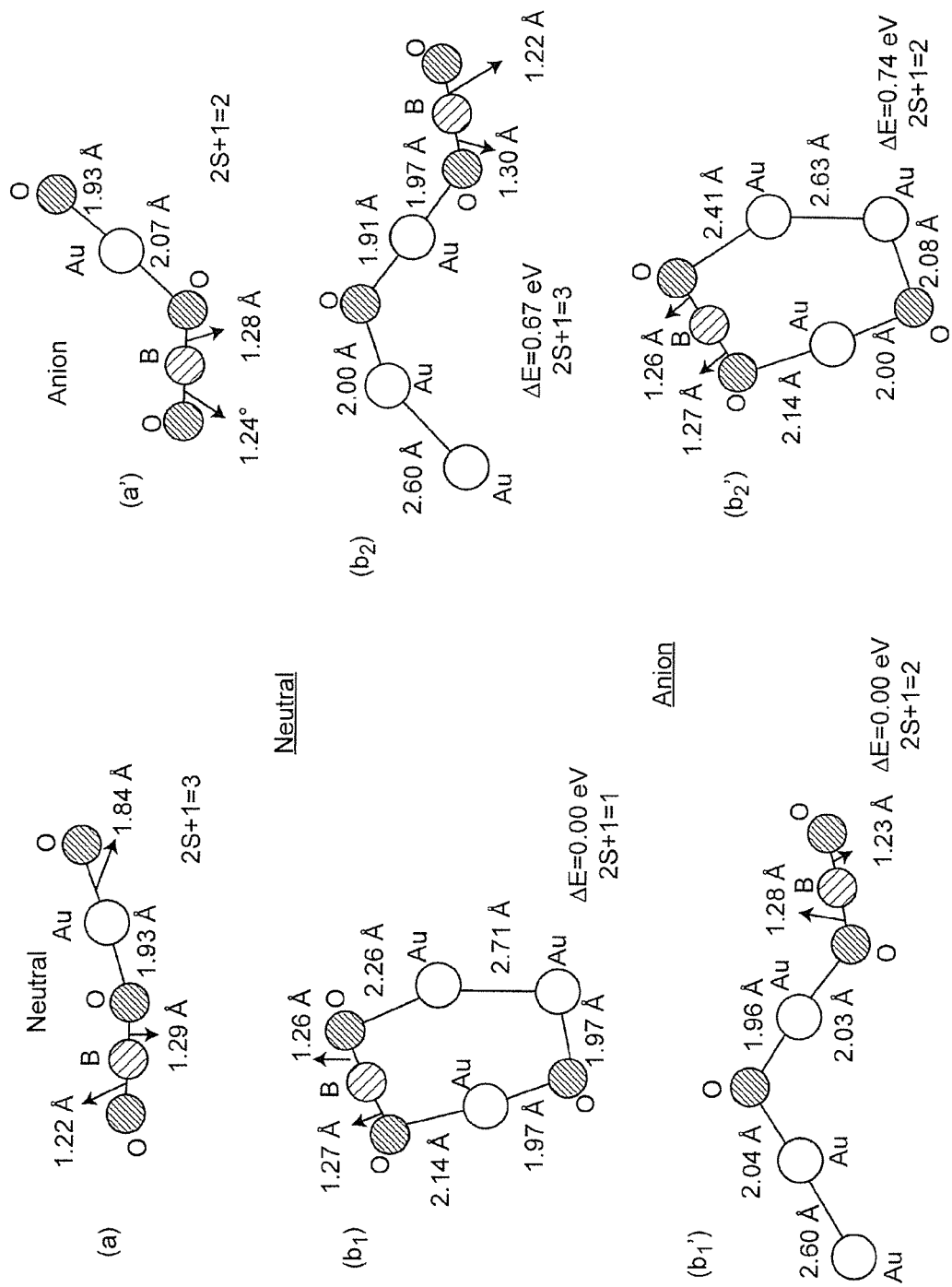
FIG. 3 depicts geometries of neutral and negatively charged $[AuO(BO_2)]$ and $[Au_3O(BO_2)]$ clusters.

We now address the structure and electron affinity of the AuO(BO$_2$) cluster which is formed when one of the O atoms of AuO$_2$ is replaced by a BO$_2$ molecule. Here the O atom can either bind to Au forming AuO(BO$_2$) or to BO$_2$ forming Au(BO$_3$) cluster. The ground state geometries of the neutral and anionic AuO(BO$_2$) cluster are shown in FIGS. 3 (a) and ($a'$), respectively. In both cases, the structure of the $BO_2$ moiety again remains intact and the O atom binds to Au. However, the B—O—Au angle increased from 128° in the anion to 160° in the neutral. The neutral $AuO(BO_2)$ cluster prefers a triplet (2S+1=3) spin multiplicity, while the anion is a doublet (2S+1=2). The singlet state (2S+1=1) of the neutral $AuO(BO_2)$ cluster is 1.34 eV higher in energy than the triplet state.

The PES of the $[AuO(BO_2)]^-$ cluster is given in FIG. 2. The calculated electron affinity of the $AuO(BO_2)$ cluster is 4.21 eV which agrees well with the experimental value of 4.0 eV. In addition, note that the first peak in the PES spectra of $[AuO(BO_2)]^-$ is broad. This is due to the structural relaxation of the resultant neutral cluster as the extra electron is removed (see FIG. 3($a$, $a'$)). The calculated VDE, which corresponds to the transition from the anionic doublet to neutral triplet state, is 4.42 eV. Note that this transition originates from the detachment of a β (spin-down) electron from the anionic doublet, thereby resulting in a triplet spin state. Our calculated VDE is in excellent agreement with the measured VDE of 4.4 eV. The next higher energy peak in the PES (in the range of 5-5.4 eV) corresponds to the electron detachment from a spin-down electron as well. We also note that the peak at ~5.6 eV in FIG. 2 can be explained as originating from the transition from the spin doublet ground state of the anion to the spin singlet excited state of the neutral. The calculated value for this transition is 5.98 eV. The $4^{th}$ energy peak in the energy range of 6-7 eV is a combination of transitions to excited state neutral triplet and singlet states. The electron affinity of the $AuO(BO_2)$ cluster is in between that of the corresponding values of $AuO_2$ and $Au(BO_2)_2$ clusters.

(b) $AuO(BO_2)$ vs $Au_3O(BO_2)$ Clusters

We investigated about creation of a hyperhalogen by manipulating the central metal core as we have shown we can do by replacing the peripheral halogen atoms by superhalogen moieties. This is accomplished by comparing the structure and properties of $AuO(BO_2)$ and $Au_3O(BO_2)$ clusters. In FIG. 3($b_1$, $b_2$, $b_1'$, $b_2'$) we show the geometries of the ground state and higher energy isomer of the neutral and anionic $Au_3O(BO_2)$ clusters. In the neutral $Au_3O(BO_2)$ cluster, the O atom inserts into the $Au_3$ cluster, thereby forming an $Au_2OAu$ segment, which in turn binds weakly to both the oxygen atoms of $BO_2$ moiety (see FIG. 3($b_1$)). In the higher energy isomer (FIG. 3($b_2$), ΔE=0.67 eV) a chain of Au—Au—O bonds is formed with O bonding to the third Au atom, which in turn is bonded to the $BO_2$ moiety. Interestingly, the spin multiplicity of the lowest energy isomer is a singlet (2S+1=1), while the higher energy isomer prefers the triplet (2S+1=3) spin state. We note that the structure of $Au_3O(BO_2)$ is entirely different from that of the iso-electronic boric acid ($BO_3H_3$) where the B at the center is attached to three O atoms which in turn are terminated with three H atoms. The ground state geometry of the $[Au_3O(BO_2)]^-$ cluster (FIG. 3($b_1'$)) is not only different from that of its neutral counterpart, but it is identical to the higher energy isomer (FIG. 3($b_2$)) of the neutral species. On the other hand, the higher energy isomer (ΔE=0.74 eV) of $[Au_3O(BO_2)]^-$ cluster (FIG. 3($b_2'$)) is identical to the ground state geometry of its neutral counterpart (FIG. 3($b_1$)). Both these anionic isomers prefer a doublet (2S+1=2) spin state. In both $AuO(BO_2)$ and $Au_3O(BO_2)$ clusters, the $BO_2$ moiety retains its structural identity. Moreover, the ground state geometry of $[Au_3O(BO_2)]^-$ can be viewed as a $[AuO(BO_2)]^-$ cluster bound to a $Au_2$.

Figure 4:
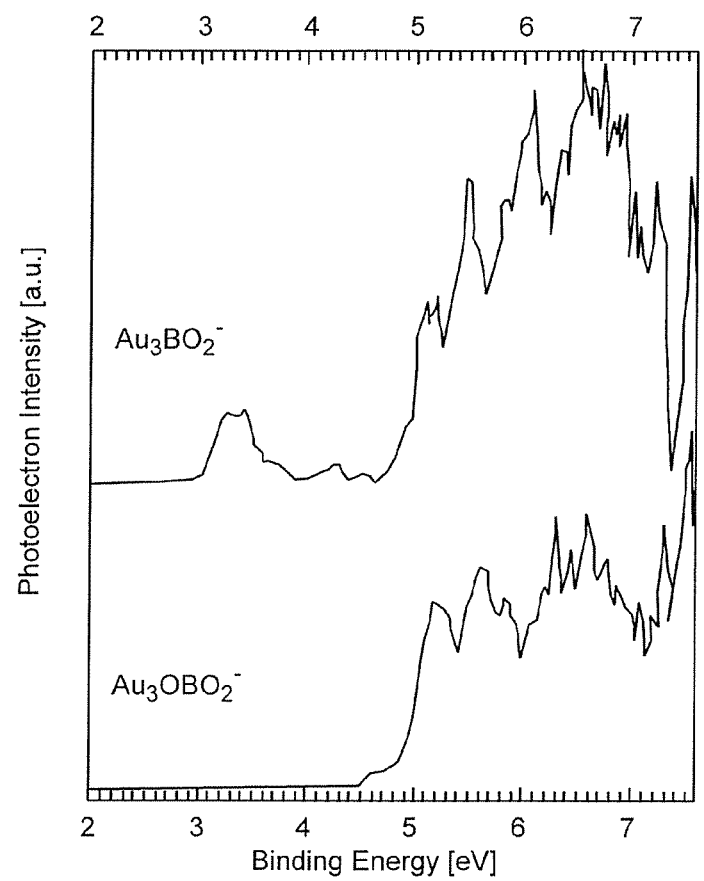
FIG. 4 is a graph which is a comparison of photoelectron spectra of $[Au_3(BO_2)]^-$ and $[Au_3O(BO_2)]^-$ clusters.

The photoelectron spectrum of the $[Au_3O(BO_2)]^-$ cluster is given in FIG. 4 and compared with that of $[Au_3(BO_2)]^-$. Introduction of an O atom into the $[Au_3(BO_2)]^-$ clusters dramatically increases the EBE to anomalously large values of 5 eV and beyond. The fact that the $[Au_3O(BO_2)]^-$ cluster is an open-shell system (doublet spin multiplicity) makes this anomalous increase of EBE even more dramatic. Most interestingly, changing the central metal core in $AuO(BO_2)$ to $Au_3O(BO_2)$ has resulted in a significant increase in the ADE and VDE values of the cluster. The large differences in the neutral and anionic ground state geometries of the $Au_3O(BO_2)$ cluster are manifested in the PES data. Our calculated VDE of 5.01 eV, resulting from the transition of the anionic doublet state to the neutral triplet state, is in very good agreement with the experimental value of 5.2 eV. However, our calculated EA of 4.19 eV does not match with the experimental ADE of 4.9 eV. This is because the resulting neutral does not automatically reach its ground state structure, but rather remains in a higher energy isomer that is structurally similar to the anionic ground state when the electron is detached from the ground state anionic cluster in the PES experiments of $[Au_3O(BO_2)]^-$. In this process, the electron detachment results in the transition to the potential energy surface of the higher energy isomer that is identical to the ground state anion, but not the ground state of the neutral species. To verify this observation further we calculated the theoretical ADE, as the energy difference between the ground state anion (FIG. 3($b_1'$) and the structurally identical higher energy neutral isomer (FIG. 3($b_2$)). This value is 4.86 eV and agrees very well with the experimental ADE (~4.9 eV). The second peak in the PES (see FIG. 4) originates from the transition of the spin doublet anion ground state to the spin singlet neutral cluster having the anion geometry. This energy is calculated to be 5.72 eV which again matches very well with the position of the second peak.

The anomalously large VDE and ADE values of $[Au_3O(BO_2)]^-$ cluster can be explained from the NBO charge analysis. In the case of the neutral cluster (FIG. 3($b_1$)), all three Au atoms lost charge to the oxygen atom and the $BO_2$ moiety, with the Au atom bound to both O and $BO_2$ leading with a charge loss of -0.881e. This charge transfer from Au atoms to two highly electronegative entities (O and $BO_2$) resulted in a total positive charge of +1.396e on the Au atoms. It is noteworthy here that in case of the $Au_3(BO_2)$ isomer, the total NBO charge on the three Au atoms was only +0.791e [21], while in the case of $AuO(BO_2)$ cluster, the total charge on the Au atom is +0.952e. In the case of the anionic cluster, the extra electron is distributed mostly on the positively charged Au atoms, with a minority of charge going to the O atom and the $BO_2$ moiety.

The distribution of the extra electron (-0.762e) over all the three Au atoms in $[Au_3O(BO_2)]^-$ resulted in a large binding energy of the extra electron, thus yielding large values of VDE and ADE. On the other hand, in the $[AuO(BO_2)]^-$ cluster, the extra electron is mostly localized on the Au (-0.392e) and the terminal O (-0.41e) bound to Au, thereby resulting in ADE and VDE values lower than that of the $[Au_3O(BO_2)]^-$ cluster. The fact that the electron affinity of $Au(BO_2)$ and $Au_3(BO_2)$ are nearly the same (see FIG. 6, Table) while that of $Au_3O(BO_2)$ is about 1 eV larger than that of $AuO(BO_2)$ suggests that the central metal core may play a role in the design of hyperhalogens, but it is not universal.

In summary the electron affinity depends on the nature of the decoration of the metal atom. A superhalogen is created when the metal atom is decorated with halogen/oxygen atoms and its electron affinity is larger than that of the constituent halogen atoms. In contrast, a hyperhalogen is created when the metal atom is decorated with superhalogens and its electron affinity is even higher than that of the constituent superhalogen. In some cases, replacing the central metal atom by a metal cluster also permits the electron affinity to increase. Similarly, by choosing different superhalogen building blocks with electron affinities larger than that of $BO_2$, hyperhalogens with even higher electron affinities can be achieved. It is also possible that if the central atom is a transition metal atom, the hyperhalogen can even carry a magnetic moment and the corresponding material could lead to a ferromagnetic insulator if these moments align in parallel. This Example has demonstrated that a new class of highly electronegative species can be designed and synthesized by tailoring both the superhalogens building blocks and the central metal core.

Methods

Experimental:

The PES experiment was conducted by crossing a mass-selected beam of negative ions with a fixed-frequency photon beam and energy analyzing the resultant photo-detached electrons. It is governed by the energy-conserving relationship, hv=EBE+EKE, where by is the photon energy, EBE is the electron binding (transition) energy, and EKE is the electron kinetic energy. Our apparatus, which has been described previously [31] consists of a Pulsed Arc Cluster Ion Source (PACTS), a time-of flight mass spectrometer for mass analysis and mass selection, an $F_2$ excimer laser operating at 7.9 eV for photo-detachment, and a magnetic bottle type electron energy analyzer. The electrodes in the PACTS source are mounted in a boron nitride cube. When oxygen was added to the carrier gas from an additional pulsed valve, we observed a strong progression of B containing $Au_nO_m$ clusters in addition to the signals of the $Au_nO_m^-$ species. The boron nitride of the cube is eroded by the $O_2$-containing plasma. Without oxygen, no boron contamination is observed in the mass spectra. We saw no peaks associated with N, even though our mass resolution of m/Δm~1000 is sufficient to distinguish nitrogen from oxygen compounds. The resulting anions were then subjected to extraction and mass analysis/selection. From the experimental photoelectron detachment data, the threshold energies and the vertical detachment energies can be estimated. The threshold energy is determined by fitting the signal increase at low binding energy to a linear function. The intersection of this line with the axis is taken as the threshold energy. If the change in the ground state geometry between the anion and the neutral is not too large, the threshold energy can be compared to the calculated electron affinity (EA) which is the energy difference between the ground states of the anion and corresponding neutral. If the geometry of anion and neutral differs significantly, then the threshold energy is compared to the calculated adiabatic detachment energies (ADE). The vertical detachment energy (VDE) is taken as the binding energy of the first maximum at lowest binding energy.

Computational:

The calculations were carried out using DFT and generalized gradient approximation (GGA) for exchange-correlation energy functional. We used the B3LYP functional and 6-311++G(3df) basis set for B and O atoms and the SDD basis for Au atoms as implemented in Gaussian 03 code [32]. The latter basis functions include scalar relativistic corrections. The equilibrium geometries of neutral and anionic $Au(BO_2)_2$, $AuO(BO_2)$ and $Au_3O(BO_2)$ clusters were calculated by optimizing various initial structures without any symmetry constraint. The stability of these clusters was confirmed by analyzing their normal mode frequencies, which are all positive.

While the invention has been described in terms of its preferred embodiments, those skilled in the art will recognize that the invention can be practiced with modification within the spirit and scope of the appended claims.

[1] Bartlett, N., Lohmann, D. H., *Proc. Chem. Soc.* 1962, 115-116.
[2] Bartlett, N., *Proc. Chem. Soc.* 1962, 218.
[3] Gutsev, G. L., Bolydrev, A. I., *Chem. Phys.* 1981, 56, 277-283
[4] Gutsev, G. L., Boldyrev, A. I., *Chem. Phys. Lett.* 1984, 108, 250-254.
[5] Gutsev, G. L., Boldyrev, A. I., *J. Phys. Chem.* 1990, 94, 2256-2259.
[6] Boldyrev, A. I., Simons, J., *J. Chem. Phys.* 1991, 97, 2826-2827.
[7] Boldyrev, A. I., W. Von Niessen, *Chem. Phys.* 1991, 155, 71-78.
[8] Boldyrev, A. I., Simons, J., *J. Chem. Phys.* 1993, 99, 4628-4637
[9] Wang, X.-B., Ding, C.-F., Wang, L.-S., Boldyrev, A. I., Simons, J., *J. Chem. Phys.* 1999, 110, 4763-4771.
[10] Alexandrova, A. N., Boldyrev, A. I., Fu, Y.-J., Yang, X., Wang, X.-B., Wang, L.-S., *J. Chem. Phys.* 2004, 121, 5709-5719
[11] Elliot, B. M., Koyle, E., Boldyrev, A. I., Wang, X.-B., Wang, L.-S., *J. Phys. Chem. A*. 2005, 109, 11560-11567.
[12] Yang, J., Wang, X.-B., Xing, X.-P., Wang, L.-S., *J. Chem. Phys.* 2008, 128, 201102-1/4.
[13] Ortiz, J. V., *Chem. Phys. Lett.* 1993, 214, 467
[14] Sobczyk, M., Sawicka, A., Skurski, P., *Eur. J. Inorg. Chem.* 2003, 3790-37977
[15] Freza, S., Skurski, P., *Chem. Phys. Lett.* 2010, 487, 19-23.
[16] Gutsev, G. L., Rao, B. K., Jena P., Wang, X. B., Wang, L.-S., *Chem. Phys. Lett.* 1999, 312, 598-605.
[17] Graudejus, O., Elder, S. H., Lucier, G. M., Shen C., Bartlett, N., *Inorg. Chem.* 1999, 38, 2503-2509.
[18] Scheller, M. K., Compton, R. N., Ceederbaum, L. S., *Science* 1995, 270, 1160-1166.
[19] Zhai, H. J., Wang, L. M., Li, S. D., Wang, L.-S., *J. Phys. Chem. A*. 2007, 111, 1030-1035.
[20] Anusiewicz, I., *Aust. J. Chem.* 2008, 61, 712-717
[21] Götz, M., Willis, M., Kandalam, A. K., Ganteför, G. F., Jena, P., *Chem. Phys. Chem.* 2010, 11, 853-858.
[22] Wang, Q., Sun, Q., Jena, P., *J. Chem. Phys.* 2009, 131, 124301-1/6.
[23] Koirala, P., Willis, M., Kiran, B., Kandalam, A. K., Jena, P., *J. Phys. Chem. C* 2010 (in press)
[24] Zhai, H. J., Burgel, C., Bonacic-Koutecky, V., Wang, L.-S., *J. Am. Chem. Soc.* 2008, 130, 9156-9167.
[25] Stolcic, D., et al., *J. Am. Chem. Soc.* 2003, 125, 2848-2849.
[26] Sun, Q., Jena, P., Kim, Y. D., Fischer, M., Ganteför, G., *J. Chem. Phys.* 2004, 120, 6510-6515.
[27] Ichino, T., Gianola, A. J., Andrews, D. H., Lineberger, W. C., *J. Phys. Chem. A* 2004, 108, 11307-11313.
[28] Schröder, D., Brown, R., Schwerdtfeger, P., Wang, X.-B., Yang, X., Wang, L.-S., Schwarz, H., *Angew. Chem. Int. Ed.* 2003, 42, 311-314.
[29] Dai, B., Yang, J., *Chem. Phys. Lett.* 2003, 379, 512-516.
[30] Klapötke, T. M., Krumm, B., Galvez-Ruiz, J.-C., Nöth, H., *Inorg. Chem.* 2005, 44, 9625-9627
[31] Burkart, S., et al, *Chem. Phys. Lett.* 1999, 301, 546-550.
[32] Gaussian 03, Revision C. 02, M. J. Frisch et al., *Gaussian, Inc., Wallingford Conn.*, 2004.

What we claim as our invention is:

1. A hyperhalogen, comprising: a metal core; superhalogens associated with said metal core, wherein the hyperhalogen has an electron affinity (EA) higher than an EA of at least one of the superhalogens included therein, wherein said superhalogens include at least one $BO_2$ and wherein the hyperhalogen has an EA of greater than 4.32 eV.

2. The hyperhalogen of claim 1, wherein the superhalogens include a plurality of superhalogens which may be the same or different and each of which is associated with said metal core.

3. The hyperhalogen of claim 2, wherein the EA of the hyperhalogen higher than the EA of each of the superhalogens.

4. The hyperhalogen of claim 1 wherein said metal core is Au-based.

5. The hyperhalogen of claim 1 wherein said metal core is Cu-based.

6. The hyperhalogen of claim 1, wherein the hyperhalogen has an EA that is 5.54 eV.

7. The hyperhalogen of claim 1 wherein said hyperhalogen is configured as a stable ternary nanocluster.

8. A composition containing a hyperhalogen of claim 1, wherein said composition is formulated in a product selected from the group consisting of a disinfectant, an air cleaner and a mood enhancer.

9. The hyperhalogen of claim 1, wherein said hyperhalogen is $Au(BO_2)_2$.

10. The hyperhalogen of claim 1, wherein said hyperhalogen is $Cu(BO_2)_2$.

* * * * *